United States Patent [19]

Sander et al.

[11] Patent Number: 4,739,097

[45] Date of Patent: Apr. 19, 1988

[54] MONOACRYLATES OF TRIHYDRIC PHENOLS AND METHOD FOR PRODUCING SAME

[75] Inventors: Juergen Sander, Liederbach; Arnold Schneller, Mainz, both of Fed. Rep. of Germany

[73] Assignee: Hoechst Aktiengesellschaft, Frankfurt am Main, Fed. Rep. of Germany

[21] Appl. No.: 896,110

[22] Filed: Aug. 13, 1986

[30] Foreign Application Priority Data

Aug. 13, 1985 [DE] Fed. Rep. of Germany ....... 3528928

[51] Int. Cl.$^4$ .................... C07C 121/50; C07C 69/76; C07C 69/00
[52] U.S. Cl. ...................................... 558/400; 560/66; 560/138; 560/141; 560/142; 560/144
[58] Field of Search ................. 560/144, 66, 142, 141, 560/138; 558/400

[56] References Cited

U.S. PATENT DOCUMENTS 4,234,733 11/1980 Isshiki et al. .................... 560/142 X

FOREIGN PATENT DOCUMENTS 2659809 7/1977 Fed. Rep. of Germany .
1226685 3/1971 United Kingdom .

*Primary Examiner*—Donald B. Moyer
*Assistant Examiner*—Patricia M. Scott
*Attorney, Agent, or Firm*—Schwartz, Jeffery, Schwaab, Mack, Blumenthal & Evans

[57] ABSTRACT

Compounds of the general formula I

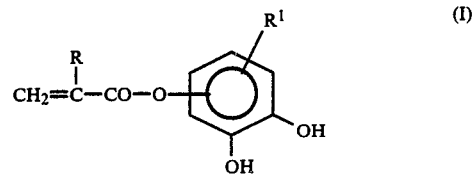

in which
R is a hydrogen or halogen atom, a cyanide or an alkyl group having 1–4 carbon atoms and
$R_1$ is a hydrogen or halogen atom, nitro, alkyl, alkoxy, aryl, aryloxy, acyl or alkoxycarbonyl group, are prepared by esterifying two adjacent OH groups to give the cyclic carbonate, esterifying the free OH group with (meth)acrylic acid and selectively hydrolyzing the carbonate. The compounds are free of polyunsaturated impurities and can be used for preparing purely linear polymers.

7 Claims, No Drawings

MONOACRYLATES OF TRIHYDRIC PHENOLS AND METHOD FOR PRODUCING SAME

BACKGROUND OF THE INVENTION

The invention relates to polymerizable esters of acrylic or methacrylic acid with polyhydric phenols and to a process for their preparation.

Monoacrylates and monomethacrylates of dihydric phenols are described in German Offenlegungsschrift No. 1,933,657 and No. 2,659,809. They are prepared by reacting dihydric phenols with for example acryloyl or methacryloyl chloride. The resulting reaction mixtures, in addition to unreacted starting compounds, contain monoacylated and diacylated phenols which can only be separated with difficulty and with yield losses. The isolated monoesters generally still contain the indicated impurities and are obtained in yields which, as a whole, are significantly below 50%, based on the starting materials. The impurities due to compounds having more than one polymerizable ester group in the molecule can lead to considerable difficulties in the further processing of the compounds to polymers, since they give rise to branched and, possibly, cross-linked polymers which have completely different solubility and viscosity properties than linear polymers.

SUMMARY OF THE INVENTION

It is accordingly an object of the invention to provide monoacrylates and monomethacrylates of trihydric phenols in a pure form.

It is another object of the invention to provide a process whereby these compounds are obtainable in a pure form and high yield.

These objects are achieved by a compound of the general formula I

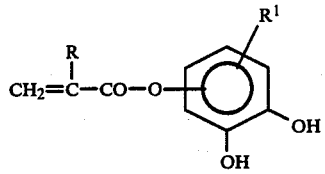

in which
R is a hydrogen or halogen atom, a cyanide or an alkyl group having 1–4 carbon atoms and
$R^1$ is a hydrogen or halogen atom, a nitro, alkyl, alkoxy, aryl, aryloxy, acyl or alkoxycarbonyl group.

The objects of the invention are further achieved by a process for preparing compounds of the above formula I, which comprises the steps of reacting a compound of the formula II

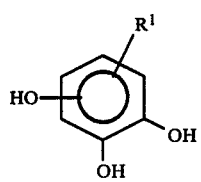

in which $R^1$ has the above-mentioned meaning, with a compound of the formula III

in which X denotes a halogen atom, an alkoxy or aryloxy group, to give a compound of the formula IV

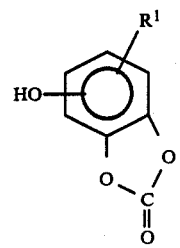

reacting the resulting compound of the formula IV with a compound of the formula V

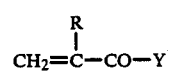

in which
Y is a halogen atom, a hydroxyl group, an alkoxy group or a radical of the formula

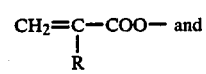

R has the above-mentioned meaning, to give a compound of the formula VI

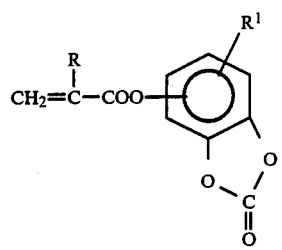

and hydrolyzing the resulting compound of the formula VI to a compound of the formula I.

DETAILED DESCRIPTION OF THE PREFERRED EMBODIMENTS

When in the above formula I R is an alkyl group, it preferably has 1 or 2 carbon atoms, particular preference being given to compounds with R=H or methyl.

When $R^1$ is a halogen atom, it can preferably be a fluorine, chlorine or bromine atom, in particular a chlorine atom. When $R^1$ is an alkyl or alkoxy group, it preferably has 1 to 6, in particular 1 to 3, carbon atoms; preferred acyl and alkoxycarbonyl groups have 2 to 15, in particular 2 to 10, carbon atoms. Aryl and aryloxy groups $R^1$ generally have 6 to 10 carbon atoms. The radical $CH_2=C(R)-COO$ can be in the 3- or 4-position relative to the two phenolic hydroxyl groups, particular preference being given to the 3-position. $R^1$ can likewise be in the 3- or 4-position.

Examples of compounds of the formula II are hydroxyhydroquinone, 5-ethylpyrogallol, pyrogallol, methyl gallate, ethyl gallate, propyl gallate, octyl gallate and dodecyl gallate. Compounds of the formula II can also be easily converted by customary halogenating and nitrating methods to the corresponding monosubstituted, disubstituted or trisubstituted chlorine, bromine, iodine and nitro derivatives.

Representatives of compounds of the formula III are phosgene, diethyl carbonate or diphenyl carbonate. When diphenyl carbonate is used, no solvent is necessary. Heating to from about 200°–300° C. gives rise to the formation of 2 moles of phenol which distill off under these reaction conditions. The purification of the cyclic carbonates of the formula IV which remain behind is effected initially through vacuum distillation and then in general through recrystallization.

In the case of using phosgene, an apolar solvent, for example toluene or xylene, is preferably used. Phosgene is customarily passed in with ice-cooling in the presence of 2 moles of a base such as pyridine, dimethylaniline or triethylamine. After the customary working-up with acid and water it is likewise possible to obtain compounds of the formula IV by removing the solvent, and to purify them by recrystallization.

Compounds of II and III are usually reacted with each other in a molar ratio of from about 0.8:1.2 to about 1.2:0.8, preferably from about 0.9:1.1 to about 1.1:0.9. When compounds of the formula II are reacted with carbonic acid derivatives of the formula III in a different molar ratio, the yields decrease, since if, in the case of using less than the stated amount of carbonic acid derivative, still unreacted starting material is present while in the case of using more than the stated amount of carbonic acid derivative, the free hydroxyl group on reaction products of the formula IV further reacts with the excess reagent to give intermolecular or intramolecular byproducts.

Preferred compounds of the formula V are acryloyl chloride, methacryloyl chloride or methacrylic anhydride. Further representatives are for example acrylic acid, methacrylic acid, 2-ethylacrylic acid and 2-butylacrylic acid and also their methyl and ethyl esters.

The esterification of compound IV must be carried out in such the way that the carbonate grouping is preserved as a protective group. This is achieved for example by reacting acryloyl or methacryloyl chloride in aprotic solvents such as chlorohydrocarbons, for example methylene chloride, chloroform, carbon tetrachloride, or aromatic hydrocarbons, for example toluene or xylene, in the presence of bases such as triethylamine. It is also advantageously possible to use the less costly methacrylic anhydride in place of methacryloyl chloride. This can be done in the presence of bases or even in the presence of acids, for example concentrated sulfuric acid. In the case of using acrylic acid and methacrylic acid or their methyl or ethyl esters, it is also possible to effect direct esterification or transesterifications under the acid or neutral conditions.

The reaction products of the formula VI prepared in this way are in general crystalline and can easily be purified by recrystallization. They are then preferably hydrolyzed in water within the temperature range of 50°–100° C. In the course of the hydrolysis, the two hydroxyl groups protected as cyclic carbonate are set free.

The elimination of the carbonate protective group must be effected in such a way that the unsaturated ester grouping is preserved. This is achieved in a preferred variant in a neutral aqueous medium. In this context, it has been found to be advantageous to regulate the amount of water used for hydrolysis in such a way that a clear solution forms when hot and, after cooling down, the compounds of the formula I crystallize out completely. Using this process they are obtained with an overall yield of at least 50%. The process described can be applied to any trihydroxyaromatic which has two alpha-position hydroxyl groups.

To prepare polymers, the new monomers can be either homopolymerized or even copolymerized with other ethylenically unsaturated monomers, in the conventional manner by means of heat, radiation and catalysts, for example peroxides or azo compounds.

The processing of the compounds according to the invention into polymers and their use as binders in light-sensitive mixtures is described in copending, concurrently filed U.S. patent application No. 896,250; the contents of which are hereby incorporated by reference.

The following preparative examples illustrate the invention.

EXAMPLE 1

Preparation of 1,2-dihydroxy-3-methacryloyloxybenzene

In a flask with a distillation attachment, 504 g of pyrogallol and 816 g of diphenyl carbonate are thoroughly mixed and gradually heated to 250° C. After complete removal of the resulting phenol by distillation, the residue is distilled in vacuo and recrystallized from toluene. This gives 490 g of 1-hydroxy-2,3-carbonyldioxybenzene (81% of theory).

The product is then dissolved in a mixture of 25 ml of concentrated sulfuric acid in 2.5 l of toluene. This solution has added to it at room temperature 496 g of methacrylic anhydride in the course of 2 hours, and the mixture is stirred at room temperature for 12 hours and is then washed repeatedly with water. The organic phase is freed from the solvent. The remaining residue becomes crystalline after addition of diisopropyl ether. The crystalline precipitate is filtered off with suction and washed with the diisopropylether, leaving 475 g of 1-methacryloyloxy-2,3-carbonyldioxybenzene (67% of theory).

This product is stirred at 65° C. in 3 l of water for 2 hours. $CO_2$ evolves to leave a clear solution. After cooling down, the resulting crystals are filtered off with suction and recrystallized from toluene. This gives 385 g of analytically pure 1,2-dihydroxy-3-methacryloyloxybenzene (92% of theory) having a melting point of 100°–102° C.

The total yield, based on pyrogallol, is 50% of theory.

EXAMPLE 2

Preparation of 1,2-dihydroxy-3-acryloyloxybenzene

Into a mixture of 125 g of pyrogallol in 400 g of toluene and 150 g of pyridine are passed with ice-cooling 99 g of phosgene. Twelve hours of stirring at room temperature is followed by heating at 100° C. for one hour. After cooling down, the reaction mixture is acidified and washed with water. The solvent is removed. The residue is recrystallized from toluene. This gives 123 g of 1-hydroxy-2,3-carbonyldioxybenzene (81% of theory).

This product is dissolved in a mixture of 81 g of triethylamine and 0.7 l of toluene. To this solution are added with ice-cooling in the course of 3 hours, 73 g of acryloyl chloride, and the mixture is stirred at room temperature for 12 hours. The organic phase is first washed with water then freed from solvent. The remaining residue is recrystallized from diisopropyl ether. This gives 130 g of 1-acryloyloxy-2,3-carbonyldioxybenzene (78% of theory).

This product is stirred at 65° C. in 0.8 l of water for 1.5 hours. $CO_2$ evolves to leave a clear solution. The crystals precipitated on cooling down are filtered off with suction and dried. This gives 94 g of 1,2-dihydroxy-3-acryloyloxybenzene (83% of theory) having a melting point of 92°–95° C.

The total yield, based on pyrogallol, is 52% of theory.

EXAMPLE 3

Preparation of ethyl 3,4-dihydroxy-5-methacryloyloxybenzoate.

In a flask with a distillation attachment, 198 g of ethyl gallate and 204 g of diphenyl carbonate are thoroughly mixed and gradually heated to 250° C. After complete removal of the resulting phenol by distillation, the residue is distilled in vacuo and recrystallized from ethyl acetate. This gives 183 g of ethyl 3-hydroxy-4,5-carbonyldioxy-benzoate (82% of theory).

This product is dissolved in a mixture of 82 g of triethylamine in 800 ml of toluene. To this solution are added in the course of 3 hours with ice-cooling, 86 g of methacryloyl chloride, and the mixture is stirred at room temperature for 12 hours. The organic phase is first washed with water and then freed from solvent. The remaining residue is recrystallized from diisopropyl ether. This gives 191 g of ethyl 3-methacryloyloxy-4,5-carbonyldioxybenzoate (80% of theory).

This product is stirred at 65° C. in 1.2 l of water for 5 hours until a clear solution is formed. After cooling down, the precipitated crystals are filtered off with suction and recrystallized from toluene. This gives 146 g of ethyl 3,4-dihydroxy-5-methacryloyloxybenzoate (84% of theory) having a melting point of 106°–108° C.

The total yield, based on ethyl gallate, is 55% of theory.

EXAMPLE 4

1,2-dihydroxy-4-methacryloyloxybenzene having a melting point of 112°–114° C. is prepared analogously to Examples 1–3.

What is claimed is:

1. A compound consisting essentially of a monoester of the formula I in a pure form

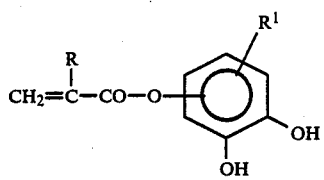

wherein
R is hydrogen or halogen, a cyano group or an alkyl group having from 1 to 4 carbon atoms;
$R^1$ is hydrogen or halogen, a nitro, alkyl, alkoxy, carbocyclic aryl having from 6 to 10 carbon atoms, carbocyclic aryloxy having from 6 to 10 carbon atoms, acyl having from 2 to 15 carbon atoms or alkoxycarbonyl having from 2 to 15 carbon atoms group; and
$R^1$ and the radical $CH_2=CR-COO-$ are in the 3 and 4 positions relative to the two hydroxyls.

2. A compound as claimed in claim 1, wherein said acyl comprises from 2 to 10 carbon atoms.

3. A compound as claimed in claim 1, wherein said alkoxycarbonyl comprises from 2 to 10 carbon atoms.

4. A compound as claimed in claim 1, wherein said compound further comprises at least one additional ring substituent comprising a chloro, bromo, iodo or nitro substituent.

5. A monoester of trihydric phenol of formula I in a pure form

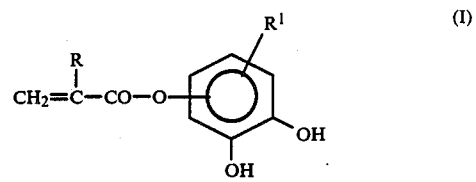

wherein
R is hydrogen or halogen, a cyano group or an alkyl group having from 1 to 4 carbon atoms;
$R^1$ is hydrogen or halogen, a nitro, alkyl, alkoxy, carbocyclic aryl having from 6 to 10 carbon atoms, carbocyclic aryloxy having from 6 to 10 carbon atoms, acyl having from 2 to 15 carbon atoms or alkoxycarbonyl having from 2 to 15 carbon atoms group; and
$R^1$ and the radical $CH_2=CR-COO-$ are in the 3 and 4 positions relative to the two hydroxyls, produced by:
reacting a compound of the formula II

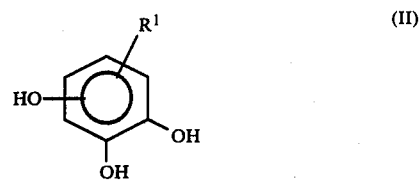

with a compound of the formula III

wherein X is halogen or an alkoxy or aryloxy group, to give a compound of the formula IV

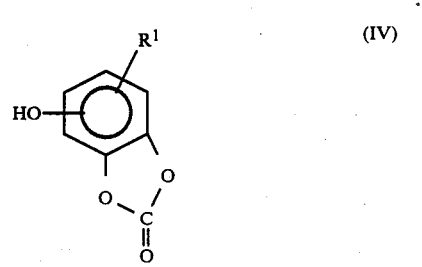

reacting the resulting compound of the formula IV with a compound of the formula V

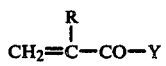 (V)

wherein Y is halogen, a hydroxyl group, an alkoxy group or a radical of the formula

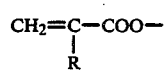

to give a compound of the formula VI

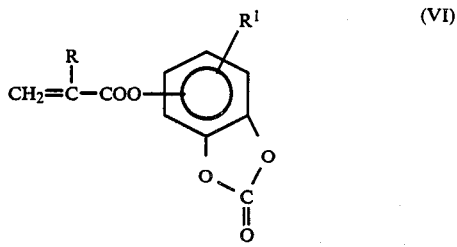

and hydrolyzing the resulting compound of the formula VI to a compound of the formula I.

6. A product produced by the method as defined by claim 5, wherein said compound of the formula II further comprises at least one additional ring substituent comprising a chloro, bromo, iodo or nitro substituent.

7. A compound as claimed in claim 1, wherein the radical $CH_2=CR-COO-$ is in the 3-position relative to the two hydroxyls.

* * * * *